(12) United States Patent
Gill (10) Patent No.: US 11,369,759 B2
(45) Date of Patent: Jun. 28, 2022

(54) HEATING ASSEMBLY FOR A VAPOUR GENERATING DEVICE (71) Applicant: JT International S.A., Geneva (CH)

(72) Inventor: Mark Gill, London (GB)

(73) Assignee: JT International S.A.

( * ) Notice: Subject to any disclaimer, the term of this patent is extended or adjusted under 35 U.S.C. 154(b) by 119 days.

(21) Appl. No.: 16/757,069

(22) PCT Filed: Dec. 28, 2018

(86) PCT No.: PCT/EP2018/097072
§ 371 (c)(1),
(2) Date: Apr. 17, 2020

(87) PCT Pub. No.: WO2019/129843
PCT Pub. Date: Jul. 4, 2019

(65) Prior Publication Data
US 2020/0245686 A1 Aug. 6, 2020

(30) Foreign Application Priority Data

Dec. 29, 2017 (EP) ...................................... 17211201
Dec. 27, 2018 (TW) ................................. 107147310

(51) Int. Cl.
*A24F 13/00* (2006.01)
*A61M 11/04* (2006.01)
(Continued)

(52) U.S. Cl.
CPC ......... *A61M 11/042* (2014.02); *A24F 40/465* (2020.01); *A24F 40/485* (2020.01);
(Continued)

(58) Field of Classification Search
CPC ....................................................... A24F 47/00
(Continued)

(56) References Cited

U.S. PATENT DOCUMENTS

2017/0055574 A1 3/2017 Kaufman et al.
2017/0135406 A1* 5/2017 Reevell .................. A24F 40/50

FOREIGN PATENT DOCUMENTS

EP 2468117 A1 6/2012
EP 3066941 A1 9/2016
(Continued)

OTHER PUBLICATIONS

International Search Report with Written Opinion for Application No. PCT/EP2018/097072 dated Mar. 29, 2019, 16 pages.

*Primary Examiner* — Phuong K Dinh
(74) *Attorney, Agent, or Firm* — Lerner, David, Littenberg, Krumholz & Mentlik, LLP (57) ABSTRACT

A heating assembly for a vapour generating device includes a heating device arranged to heat, in use, a body, the body including a vaporisable substance located in use in a heating compartment of the heating assembly, the heating assembly being arranged to supply, in use, power to the heating device to heat the body; a temperature sensor arranged to monitor, in use, a temperature related to heat generated from the body, temperature information related to heat generated from the body being determinable from the monitored temperature; and a memory accessor arranged to access, in use, a memory that holds a relationship between the temperature information, the amount of power supplied to the heating device or the profile of power supplied to the heating device, and at least one condition including an age of the body, or a type of the body, or the presence of the body.

19 Claims, 6 Drawing Sheets

(51) Int. Cl.
*A24F 40/53* (2020.01)
*A24F 40/465* (2020.01)
*A24F 40/57* (2020.01)
*G05B 19/042* (2006.01)
*A24F 40/485* (2020.01)
*A24F 40/51* (2020.01)
*A61M 15/06* (2006.01)
*A24F 40/20* (2020.01)

(52) U.S. Cl.
CPC .............. *A24F 40/51* (2020.01); *A24F 40/53* (2020.01); *A24F 40/57* (2020.01); *A61M 15/06* (2013.01); *G05B 19/042* (2013.01); *A24F 40/20* (2020.01); *G05B 2219/2658* (2013.01)

(58) Field of Classification Search
USPC .................................................. 131/328–329
See application file for complete search history.

(56) References Cited

FOREIGN PATENT DOCUMENTS

| | | |
|---|---|---|
| GB | 2537121 A | 10/2016 |
| WO | 2016075436 A1 | 5/2016 |

* cited by examiner

HEATING ASSEMBLY FOR A VAPOUR GENERATING DEVICE

CROSS-REFERENCE TO RELATED APPLICATIONS

The present application is a national phase entry under 35 U.S.C. § 371 of International Application No. PCT/EP2018/097072, filed Dec. 28, 2018, published in English, which claims priority to European Application No. 17211201.3 filed Dec. 29, 2017 and to Taiwanese Application No. 107147310 filed Dec. 27, 2018, all of the disclosures of which are incorporated herein by reference.

BACKGROUND

The present invention relates to a heating assembly for a vapour generating device.

Devices which heat, rather than burn, a substance to produce a vapour for inhalation have become popular with consumers in recent years.

Such devices can use one of a number of different approaches to provide heat to the substance. One such approach is that of simple provision of a heating element to which electrical power is provided to heat the element, the element in turn heating the substance to generate vapour.

Although a number of ways to generate vapour exist, one way to achieve such vapour generation is to provide a vapour generating device which employs an inductive heating approach. In such a device an induction coil (hereinafter also referred to as an inductor and induction heating device) is provided within the device and a susceptor is provided within the vapour generation substance. Electrical energy is provided to the inductor when a user activates the device which in turn creates an electromagnetic (EM) field. The susceptor couples with the field and generates heat which is transferred to the substance and vapour is created as the substance is heated.

Using induction heating to generate vapour has the potential to provide controlled heating and therefore controlled vapour generation. However, in practice such an approach can result in unsuitable temperatures unknowingly being produced in the vapour generation substance. This can waste power making it expensive to operate and risks damaging components or making ineffective use of the vapour generation substance inconveniencing users who expect a simple and reliable device. These issues also apply when generating vapour through heating other than through induction heating.

This has been previously addressed by monitoring and controlling temperatures in a device. However, factors other than just temperature, such as length of use, also affect performance and how efficiently vapour is able to be generated.

The present invention seeks to mitigate at least some of the above problems.

SUMMARY OF INVENTION

According to a first aspect, there is provided a heating assembly for a vapour generating device, the heating assembly comprising: a heating device arranged to heat, in use, a body, the body comprising a vaporisable substance located in use in a heating compartment of the heating assembly, the heating assembly being arranged to supply, in use, power to the heating device to heat the body or being arranged to supply, in use, power based on a predetermined power supply profile, said power supply profile being configured to provide a predetermined heating profile to the body; a temperature sensor arranged to monitor, in use, a temperature related to heating at the body, temperature information related to heating at the body being determinable from the monitored temperature; and a memory accessor arranged to access, in use, a memory that holds a relationship between the temperature information, the amount of power supplied to the heating device or the profile of power supplied to the heating device, and at least one condition, the at least one condition including an age of the body, or a type of the body, or the presence of the body.

This allows characteristics of the body to be determinable based on the power usage and the monitored temperature. We have found that these characteristics have an effect on the performance of the assembly (e.g. the device together with the body) during use. Accordingly, being able to determine characteristics of the body allows a used body to be exchanged for an unused body before or when the characteristics of the used body have reached a stage where the performance, efficiency and safety of the assembly is deteriorating. Note that in some embodiments, the stored relationship data may not explicitly or clearly reference a condition named as an age of the body, or a type of the body, or the presence of the body. Nonetheless, so long as the relationship data is substantially linked to a specific relationship between the temperature information and the amount of power supplied to the heating device which corresponds to an age of the body, or a type of the body, or the presence of the body, such embodiments are naturally intended to fall within the scope of the present invention.

By "profile of power supplied to the heating device", it is intended to mean the manner in which the power is provided to the heating device, for example taking into account the rate of change of the power supplied, and/or the amount of time over which power is provided to the heating device. For example, the amount of power, or rate of power delivery may be the same, but the power may be supplied over a period of 1 second or over a period of 3 seconds, which may resulting in the body being heated to a different temperature. By using the profile of power supplied to the heating device to allow the at least one condition of the body to be detected, it is possible to apply a predetermined heating amount or heating profile to the body during its use that is suitable for said at least one condition of the body. The heating profile for example may correspond to the body being heated to predetermined temperature, at a predetermined rate of increase of temperature or for a predetermined time.

The temperature sensor may be a thermistor or a thermocouple. For example, the temperature sensor may be a resistance temperature detector, such as a resistance temperature detector, which may use a platinum resistor as a sensing element. The platinum resistor may be a platinum film (e.g. a thin film) on a ceramics substrate, which may be passivated by glass coating. The temperature sensor may for example be a PT100 from Measurement Specialties, Inc of the PTF family of sensors.

Preferably the vaporisable substance is a solid or semi-solid material, the body thereby comprising a vaporisable substance of solid or semi-solid material.

The assembly may be arranged to obtain, in use, the temperature information. The temperature information may be generated or determined by a controller of the heating assembly, the temperature sensor or by an external processing unit. The temperature information may be generated or determined by processing the monitored temperature, such as by recording the monitored temperature over a predetermined time period and analysing the recorded monitored temperature for trends including, for example, rate of change, increase, decrease, variation or a number of other factors. The power usage of the heating device and/or power supplied to the heating device may also be monitored and/or recorded and/or determined by the heating device, the controller or the external processing unit.

The temperature information may include the monitored temperature itself or any other pertinent information able to be obtained from monitoring the temperature. Typically, the temperature information includes a rate of change of the monitored temperature. The rate of change of temperature allows the speed at which the temperature of the body is increasing to be known. We have found that this is a useful piece of information for ascertaining the age of the body due to differences in how quickly a body heats up as moisture levels in the body decrease through usage.

Additionally or alternatively, temperature information may include a surface temperature of the body. Having the surface temperature of the body available is also useful. This is because we have found that different body types warm to different temperatures for the same amount of power usage. As such, this assists with identifying the body type. Additionally, this assists with determining age of a body because, for a particular amount of power usage, we have found that a more used body reaches a higher (surface) temperature than a less used body.

One example of the monitored temperature may also be a surface temperature of the body.

The at least one condition may be determinable from the temperature information and the amount of power supplied to the heating device or the profile of power supplied to the heating device based on the relationship held in the memory.

The at least one condition may be determinable based on any aspect of the temperature information. As an example, where the heating profile corresponds to the body being heated to predetermined temperature (which may correspond to the temperature information), based on the "heating profile" (e.g. the profile of power supplied to the heating device), the at least one condition can be detected.

Typically, the at least one condition is able to be determined based on a threshold temperature for the temperature information, and preferably, there are a plurality of threshold temperatures, at least one threshold temperature determining the age of the body, at least one threshold temperature determining the type of the body, and at least one threshold temperature determining the presence of the body.

We have found that a threshold temperature which a body potentially reaches allows a distinction to be drawn between characteristics of a body. Setting a threshold simplifies the determination of the at least one condition of the body since it enables a binary choice to be made. This reduces the amount of processing that needs to be carried out to determine the at least one condition therefore reducing the amount of power required to determine the at least one condition.

In certain embodiments, only one of the at least one condition is determined at any one time. However, typically at least two of the age of the body, the type of the body and the presence of the body are determinable at the same time. This makes the determination more efficient as multiple conditions are able to be determined in a single determination process. This reduces the amount of power used to determine multiple conditions therefore saving power.

The vapour generating device may further comprise a controller arranged to determine, in use, temperature information related to heating at the body.

The controller may use the temperature information in any way considered suitable. Typically, based on the temperature information, the controller is arranged to determine, in use, a next action of the heating assembly. This allows a feedback loop to be established meaning the controller is able to react to up to date temperature information and to adjust what the assembly does in reaction to any changes detected. This has the advantage of making power use more efficient because only minor adjusts will need to be made during use, which will require low levels of power use, or small changes in power use, instead of larger changes due to an extreme situation occurring which require a large amount of power to address.

The next action may be any action capable of being carried out by the controller or assembly. Typically, based on the relationship held in the memory, the controller is arranged to prohibit, in use, supply of power to the heating device when an age of the body is greater than a threshold age, and is arranged to supply, in use, power to the heating device when the age of the body is less than the threshold age or when a type of the body is determined to be an unsuitable type. This reduces power wastage and improves safety because the threshold age can be set to a suitable age where the temperatures to which the body is heated are kept within levels that are safe for the user and do not damage the assembly and also avoid any inefficient heating situations that may occur as the body ages.

The assembly may operate in any suitable manner. Typically, the heating assembly has a first power supply mode and a second power supply mode, and wherein the first power supply mode is arranged to be applied, in use, when heating the body, and the second power supply mode is arranged to be applied, in use, after the first power supply mode is applied, to maintain the body at a temperature within a predetermined temperature range, preferably when in the first power supply mode, the heating assembly is arranged to provide at least 80 percent (%) of full power to the heating device. This allows the at least one condition of the body to be detected based on power usage and temperature information obtained whilst the assembly is operating in one mode, but also provides a further mode where the processing corresponding to determining the at least one condition of the body need not be carried out. Since carrying out the determination requires processing to be conducted, which uses power, having a power supply mode that does not involve the determination being conducted thereby reduces the power usage attributable to said determination.

This also allows a user to enjoy smoking as soon as possible after they start using the device (such as seeking to draw a puff from the device) and allows the device to be maintained within a predetermined temperature after the temperature reaches the predetermined temperature under effective power usage.

This means the assembly of this aspect may relate to devices using solid vaporisable substance, hereafter referred to as a "solid-vapour device", instead of devices using liquid vaporisable substance, hereafter referred to as a "liquid-vapour device". Solid vapour devices produce vapour by heating tobacco, tobacco products or other such solid vaporisable substances, whereas liquid-vapour devices produce vapour by heating a liquid.

In both types of device, to use the device, a user draws vapour from the device. This is referred to as a "puff" as the device typically provides a puff of vapour from a mouthpiece. To produce vapour for a puff, the vaporisable substance is heated. This is common to solid-vapour devices and liquid-vapour devices.

Users typically use a device for a time period of their choosing over which they draw several puffs from the device regardless of the type of the device. This period of use of the device producing one or more puffs is referred to as a "session". Each session therefore has a first puff at the start of the session and generally has further puffs.

The energy requirements to produce the first puff are different for solid-vapour devices than for liquid-vapour devices.

One of assumption is that due to an ability for liquid vaporisable substance to move towards a heating device during use such that only a small amount of liquid needs to be vaporised (ideally just enough for one puff), but this not being possible for solid vaporisable substances, a heating device in a solid-vapour device needs to provide more heat to be able to heat a much larger amount of the solid vaporisable substance (e.g. the whole portion) which would also typically tend to be further from the heating device. This of course requires more energy and time as the heat must be transmitted further from the heating device. This means that in such solid-vapour devices, in general, more power and time is required than for a liquid-vapour device for the first vapour to be output during a puff when the vaporisable substance is heated from the same temperature (normally ambient temperature). As a demonstration of this, in general, solid-vapor devices currently need several seconds or more after starting heating before vapour is generated, whereas liquid-vapour devices can generate vapour almost at the same time as starting to provide heating.

In general, in liquid-vapour devices, power is only supplied to a heating device when a user actively draws a puff from the device. On the other hand we have found that in solid-vapour devices, power may be supplied to a heating device (in the case of the assembly of the first aspect, to the heating device) at any time after the assembly is switched on. By providing heating in such a manner, this means that after a vaporisable substance has reached a temperature that causes the substance to vaporise, i.e. a vaporisation temperature or target operational temperature, for example, after the first power supply mode, vapour continues to be generated regardless of whether a user is drawing a puff. This also allows a user to actively draw on the mouthpiece and to be provided with vapour at any time during a session, for example, during the second power supply mode. This is in line with a conventional cigarette.

We have found that by providing continuous heating during a session, an energy saving is achieved. This is because it generally requires more energy to re-heat a solid vaporisable substance that has been allowed to cool below the target operational temperature than it does to maintain the solid vaporisable substance at the target operational temperature. Further, by maintaining the temperature for later puffs, a user can draw vapour from the device in a puff at any time without waiting as they may need to do for the first puff.

Accordingly, in relation to the first aspect typically, the heating device is arranged in use to heat the vaporisable substance during a period where a user is drawing air through a mouthpiece of the assembly. In this case by "period" it is intended to mean a session, meaning that heating is being provided over the whole of the length of the session. In some circumstances however, "period" could be intended to mean only during the time when a user is actively drawing air/gas/vapour/aerosol through the mouthpiece.

Since the user is able to choose when to actively draw on the device, the time between draws in a session is likely not to be regular. During a session, if the gap between draws is too long, the amount of energy used by a solid-vapour device maintaining the vaporisable substance at the target operational temperature will be higher than allowing the vaporisable substance to cool and be re-heated. As long as the gap between occasions when the user actively draws on the device is not too long, the energy saving advantage set out above is achieved. To avoid the efficiency gains being lost, the session in a solid-vapour device may "time out" by stopping heating after a predetermined time period, requiring a session to be re-started when the user next wishes to draw on the device.

Accordingly, in relation to the first aspect, the heating device may be arranged in use to end heating of the vaporisable substance if the time period since the last draw of air through the mouthpiece by a user is greater than a predetermined time period. Air passage through the mouthpiece by a user may be detectable by a sensor in the device, such as a temperature sensor or pressure sensor, such as a (pressure-based) puff sensor. For example, the temperature sensor may detect temperature fluctuations when a user causes passage of air through the mouthpiece (and heating compartment).

Once the temperature information has been obtained, at least one condition may be determinable from the temperature information and the amount of power supplied to the heating device in the first power supply mode or the profile of power supplied to the heating device based on the relationship held in the memory.

This allows the controller to decide on the next step of how to heat as soon as possible, e.g. the heat profiling in the later part of the first mode and/or the second mode can be determined based on the detected condition. Further in the first power supply mode, a large amount of power is supplied in a short time period. As such, it is beneficial for controller to determine the at least one condition more easily and accurately in a short time period.

Additionally, it may be possible to determine useful information from the rate of increase of detected temperature during the first power supply mode while the body is heating up towards the target temperature. For example, if the body contains a significant amount of water, for example greater than 5%, then it may be possible to detect a reduction in the rate of increase of the (surface) temperature of the body at about 100° C. as the water present in the body starts to vaporise at about this temperature, causing energy to be consumed in vaporising the water rather than it increasing its temperature. The amount of water contained in the body may be an indicator of the amount of time that the body has been stored in an ambient environment having significant humidity without the benefit of protective packaging. Such water content may also be detrimental to the quality of vapour produced by the assembly. It may therefore be beneficial to cease heating the body and advise the user to dispose of the body and replace it with a new, fresh (for example, unused) body, or else to advise the user to wait until commencing vapour and to continue to heat the body at a reduced temperature (sufficient to vaporise all or most of the excess water) until most of the (excess) water has been vaporised and then to heat the body to the operating temperature. Other constituents may also be detectable in this way, or other characteristics of the body may be determinable based on the particular temperature ramp up profile.

The first power supply mode may be arranged to occur at any time. Typically, the first power supply mode is arranged to occur in response to a trigger, the trigger being determined based on a change in the monitored temperature or a change in a switch caused by action of a user, such as a motion for changing the body (e.g. opening lid of compartment) or switch on for start smoking session. This allows the first power supply mode to be used when a body first heated after it is placed in the heating compartment. This is beneficial because information about the body is gathered as soon as possible instead of after use when certainty about the state of the body when first inserted into the heating compartment is decreased. The controller may be arranged to apply, in use, a respective power supply mode in response to a trigger or in response to a predetermined sequence, such as the second power supply mode being applied after the first power supply mode is applied preferably when predetermined conditions, such as those referred to above, occur. The trigger may indicate a change of body in the heating compartment.

The heating assembly may further comprise an indicator arranged to display, in use, at least one property of the detected at least one property. This allows a user to be informed of the condition of the body being used and improves their awareness of the experience they are likely to achieve with the body currently in use and how it may affect the usage and safety of the device.

The heating assembly may be an induction heating assembly, the heating device may be an induction heating device, and the body may further comprise an induction heatable susceptor, the induction heating device being arranged to heat, in use, the induction heatable susceptor of the body, the heating assembly being arranged to supply, in use, power to the induction heating device to heat the induction heatable susceptor; the temperature sensor being arranged to monitor, in use, a temperature related to heat generated from the susceptor, temperature information related to heat generated from the susceptor being determinable from the monitored temperature.

By using induction heating, the heat is generated within the body, and only when the susceptor is present. As such, the heating is more efficient because it is generated within the body instead of having to be transferred to the body, for example, by conduction away from the heating device (which would also cause heating of components other than the body). Additionally, heating by induction improves safety because no heat will be generated without there being a suitable body located in the heating compartment to heat. This also avoids heating being applied needlessly or by accident when no suitable body is present in the heating compartment.

The susceptor may comprise one or more, but not limited, of aluminium, iron, nickel, stainless steel and alloys thereof, e.g. nickel chromium. With the application of an electromagnetic field in its vicinity, the susceptor may generate heat due to eddy currents and magnetic hysteresis losses resulting in a conversion of energy from electromagnetic to heat.

When using induction heating, the assembly may include a fluctuating electromagnetic field generator, for example in the form of an induction heating coil and associated driving circuitry and a power source, arranged to operate in use to generate a fluctuating electromagnetic field having a magnetic flux density of between approximately 0.5 T and approximately 2.0 T at the point of highest concentration.

The power source and circuitry may advantageously be configured to operate at a high frequency whereby it may drive an induction heating coil of the heating device at a similarly high frequency. Preferably, the power source and circuitry may be configured to operate at a frequency of between approximately 80 kHz and 500 kHz, preferably approximately 150 kHz and 250 kHz, more preferably approximately 200 kHz. Preferably, in embodiments including an induction heating coil, the power source drives the induction coil at the same frequency (i.e. between approximately 80 kHz and 500 kHz, preferably approximately 150 kHz and 250 kHz, more preferably approximately 200 kHz).

Whilst the induction coil, which is one form the induction heating device may take, may comprise any suitable material, typically the induction coil may comprise a Litz wire or a Litz cable.

The use of induction heating provides several technical advantages in embodiments in which it is used. For example, in embodiments which require a body to include susceptors (as discussed above) in order to be heated by the device, if a body is inserted into the device which does not include a susceptor (i.e. if an unsuitable body is inserted into the device—e.g. by mistake) then it can readily be determined that no suitable body is present in the device based on the relationship between power applied to the heating device and the temperature information relating to heating at the body.

Thus, in some embodiments, a suitable body may be provided with a susceptor or susceptors having a predetermined resonant frequency. In such a case it may be possible to distinguish between suitable and unsuitable bodies based on monitoring and detecting the relationships between power applied to the heating device and temperature information when the fluctuating magnetic field generator generates fluctuating magnetic fields at the predetermined resonant frequency. In particular, in such a case, there would be an expected range of rates at which the temperature should increase to identify a suitable body for heating. In particular, too slow a rate of heating would indicate that the body did not include a suitable substrate, whereas heating too quickly could indicate either that an unsuitable susceptor is included or that the body is too old or has already been heated and is thus depleted of humectant, etc.

According to a second aspect, there is provided a method for determining a condition of a body, the body comprising a vaporisable substance, the method comprising: heating the body with a heating device by supplying power to the heatable device; monitoring a temperature related to heating at the body, temperature information related to heating at the body being determinable from the monitored temperature; accessing a memory, the memory holding a relationship between the temperature information, the amount of power supplied to the heating device or the profile of power supplied to the heating device and at least one condition, the at least one condition including an age of the body, or a type of the body, or the presence of the body, when applied said power supply profile provides a predetermined heating profile to the body; and determining the at least one condition based on the relationship held in the memory.

As with the first aspect, in the second aspect, preferably the vaporisable substance is a solid or semi-solid material, the body thereby comprising a vaporisable substance of solid or semi-solid material.

The memory may be located on an external device or may be located in the cloud, by which we mean internet based computer storage and processing resources that are accessible on demand. In such as case, the vapour generating device may have a memory accessor that is able to access and interact with the memory.

The method of the second aspect may also include that preferably on starting heating, setting a remaining heating amount for the body based on a relationship between the temperature information, the amount of power supplied to the heating device or the profile of power supplied to the heating device and age of the body in the memory.

The setting of a remaining heating amount for the body may be achieved by providing a predetermined power level for a predetermined time period and detecting the rate of increase of temperature during said time period, the detected rate being the temperature information.

Additionally, the setting of the remaining heating amount of the body may be based on the detected rate of increase of temperature during said time period, or based on data associated with the detected rate of increase of temperature such as, for example, a profile of the rate of increase of temperature of the body (e.g. identifying changes in the rate of increase of temperature at different temperatures). Further, information about the relationship between age of the body and the detected rate of increase of temperature during the period which relationship information may be held in the memory (for example in a lookup table or as a formula); and this could be used in conjunction with the detected information about the rate of increase of temperature during the heating period to determine an estimated age of the body and then the remaining heating amount for the body could be set based on the estimated age of the body.

By "heating amount" it is intended to mean the remaining amount the body can be heated before the body is considered to have expired or have been used to its full extent. A body is considered to have expired or to have been used to its full extent when a predetermined amount of vaporisable substance is left in the body, such as zero. The heating amount may be measured in amount of time remaining for which the body can be heated, or the number of draws, also referred to as "puffs", remaining before heating of the body will cause the body to expire.

By the term "vaporisable substance" we intend to mean a substance from which vapour is able to be generated. Typically the vapour may be generated by heating the vaporisable substance, but may be generated under other appropriate conditions. The vapour may be in the form of an aerosol, meaning the vaporisable substance may be an aerosol former. The vaporisable substance may itself turn into vapour under appropriate conditions (such as when heated, for example, to above a threshold temperature), or one or more constituents of the vaporisable substance may vaporise (or volatilise) into vapour under appropriate conditions. Further, the vaporisable substance may be a material imbued, soaked or interwoven with a constituent that vaporises under appropriate conditions, or be a product that undergoes a transformation process or produces a material that turns into vapour under appropriate conditions. More detail is provided below in relation to the vaporisable substance.

The "predetermined power level" applied "on starting heating" may be the first power supply mode referred to above.

Determining the remaining heating amount allows heating to be stopped before further heating becomes dangerous or would cause the body to burn or become damaged. This reduces the risk to the user and reduces the likelihood of damaging the device holding the body by overuse of the body.

Once the remaining heating amount is determined, this amount may be stored in the memory and/or a controller and preferably the remaining heating amount is monitored/detected while the user is causing the device to be used (e.g. by heating) and the controller and/or memory may determine when the remaining heating amount has elapsed. This reduces the chances of the body being over used and becoming burnt or causing damage.

Additionally, or alternatively to setting a remaining heating amount, if preferably on starting heating, a maximum permissible power level for the body may be determined based on a relationship between the temperature information, the amount of power supplied to the heating device or the profile of power supplied to the heating device and age of the body in the memory. This allows an appropriate amount of heating to be provided to the body as the amount of vaporisable substance in the body decreases over time due to age and heating. This reduces the risk of overheating the body, lowering the chances of the body being burnt by further heating.

The relationship may be between rates of increase of temperature and permissible power levels and setting a power level to be supplied to the heating device based on a permissible power level corresponding to the detected rate.

Additionally, the maximum permissible power level determination may be achieved by a predetermined power level being provided for a predetermined time period and the rate of increase of temperature is detected, the detected rate being the temperature information.

The monitored rate may also be used to determine if the body is a body compatible with the heating device based on the relationship between the temperature information, the amount of power supplied to the heating device and at least one condition, when the body is determined as being compatible heating continues, and when the body is determined as being incompatible, heating is stopped. This again reduces the risk of the body being heated from causing damage and harming the user through unsuitable heating.

When heating is stopped due to an incompatible body, an indication may be provided to the user. This alerts the user to the need to change the body. Heating may also be stopped when the remaining heating amount is determined to have been used.

Heating of the body may be started and/or stopped by a trigger. This allows greater user control of the heating, which may prolong the lifespan of the body. The trigger causing heating of the body to start may be different from the trigger causing the heating of the body to stop. The trigger causing heating of the body to start may be referred to as a "first trigger". The trigger causing heating of the body to stop may be referred to as a "second trigger". The first trigger and/or second trigger may be provided by activation of a button, such as a push button, by a user. The first trigger may be provided by a cover of a heating compartment being opened by a user. The second trigger may be provided by the cover of the hearing compartment closing. The cover may close automatically due to the cover typically having a bias to a closed position and being stopped from closing in use due to the presence of a body in the heating compartment. The second trigger may be a predetermined time period, e.g. 1 minute, 3 minutes or 5 minutes, of time elapsing since a user drew vapour from the assembly, such as by actively drawing air through a mouthpiece. Regardless of whether the trigger causing heating of the body to start and the trigger causing heating of the body to stop are different or the same, the trigger causing heating of the body to stop may be a predetermined time period having elapsed since the last puff or the activation/de-activation of a switch, such as a push of a push switch, or a touch of a touch switch.

According to a third aspect, there is provided a vapour generating device comprising: a heating assembly according to the first aspect; a heatable cartridge located within a heating compartment of the heating assembly; an air inlet arranged to provide air to the heating compartment; and an air outlet in communication with the heating compartment. The cartridge of the first aspect may be the body described in relation to the first aspect or second aspect.

The cartridge may include any suitable material. Typically, the cartridge includes humectant or tobacco containing moisture, and preferably the cartridge is a single use cartridge arranged to expire, in use, on consumption of a predetermined amount of at least one constituent of the cartridge.

The vaporisable substance would be any type of solid or semi-solid material. Example types of vapour generating solids include powder, granules, pellets, shreds, strands, porous material, foam material or sheets. The substance may comprise plant derived material and in particular, the substance may comprise tobacco.

Preferably, the vaporisable substance may comprise an aerosol-former. Examples of aerosol-formers include polyhydric alcohols and mixtures thereof such as glycerine or propylene glycol. Typically, the vaporisable substance may comprise an aerosol-former content of between approximately 5% and approximately 50% on a dry weight basis. Preferably, the vaporisable substance may comprise an aerosol-former content of approximately 15% on a dry weight basis.

Examples of solid materials which contain a liquid aerosol former which are suitable for forming the body in embodiments of this invention include tobacco rods comprising sheets of reconstituted tobacco paper impregnated with humectant, typically up to amounts of about 20% humectant by weight, the humectant typically being glycerol or a mixture of glycerol and propylene glycol, finely ground tobacco particles with humectant added to form a paste, or a tobacco mousse also formed from finely ground tobacco particles mixed with humectant, but typically also including a gel forming agent and with levels of humectant up to about 40% by weight (preferably between 20% and 40%) such as described in pending patent application WO 2018/0122375. Using bodies such as mousse with high levels of humectant (whilst still being sufficiently dry around the surface to prevent staining surfaces which they may contact) makes certain embodiments advantageous because it is possible to detect the type of such bodies without the need to provide some form of paper wrapping or packing for the body to render its type identifiable by means of a printed indication, thus being environmentally friendly in terms of minimising excess packaging matter. Additionally, such bodies having a high weight of humectant are well suited to having their state of use identified by measuring the rate of increase of their temperature under heating as this can vary considerably as the humectant is used up, especially for bodies such as mousse where the humectant is almost completely used up during vaping (going from about 40% by weight to close to zero % by weight after a full vaping session).

Upon heating, the vaporisable substance may release volatile compounds. The volatile compounds may include nicotine or flavour compounds such as tobacco flavouring.

The body may be a capsule which includes in use a vaporisable substance inside an air permeable shell. The air permeable material may be a material which is electrically insulating and non-magnetic. The material may have a high air permeability to allow air to flow through the material with a resistance to high temperatures. Examples of suitable air permeable materials include cellulose fibres, paper, cotton and silk. The air permeable material may also act as a filter. Alternatively, the body may be a vaporisable substance wrapped in paper. Alternatively, the body may be a vaporisable substance held inside a material that is not air permeable, but which comprises appropriate perforation or openings to allow air flow. Alternatively, the body may be the vaporisable substance itself. The body may be formed substantially in the shape of a stick.

According to a fourth aspect of the present invention, there is provided a body or cartridge for use with any of the preceding aspects, comprising a vaporisable substance and adapted such that at least one condition including an age of the body or capsule, a type of the body or capsule or the presence of the body or capsule, can be determined in dependence upon a relationship between power supplied to a heating device for heating the body or capsule and temperature information related to heating at the body or capsule. Preferably, the adaptation may include providing a body having a percentage of vaporizable liquid (preferably of humectant such as propylene glycol and/or glycerine, but possibly additionally including other vaporizable liquids such as water or ethanol, etc.) which is greater than 20 wt % (100 wt % is equal to the total weight of the liquid and the vaporisable substance, such as tobacco, humectant and/or plant derived material) when fresh or "young" which reduces by at least 4 wt % when the body or capsule has been heated over one session or left after removing from a packaging associated with the body or capsule for more than a predetermined period of time (of preferably at least 3 months) in predetermined environmental conditions. Most preferably, the vaporizable liquid reduces by at least 7% when heated over one session.

The adaptation to the body or capsule for the purpose of the fourth aspect of the present invention may include providing a susceptor in the body or capsule which has a heating efficiency which depends upon the frequency of an energising fluctuating magnetic field, such that it has a maximum heating efficiency at a first predetermined resonant frequency and falls to below a predetermined heating efficiency threshold of 50% of the maximum heating efficiency either side of a frequency range.

According to a fifth aspect of the present invention, there is provided a set of bodies of cartridges according to the fourth aspect of the present invention, packaged within a packaging adapted to prevent the percentage of vaporizable liquid from falling less than 3 wt % for a predetermined period of time preferably of at least one year, until the packaging is opened (e.g. by a consumer).

BRIEF DESCRIPTION OF FIGURES

An example of an induction heating assembly is described in detail below, with reference to the accompanying figures, in which.

DETAILED DESCRIPTION

We now describe an example of a vapour generating device, including a description of an example induction heating assembly, example induction heatable cartridges and example susceptors. While only heating by induction is described below, other forms of heating, such as resistive heating, exist and are able to be applied in the example vapour generating device instead of heating by induction.

Figure 1:
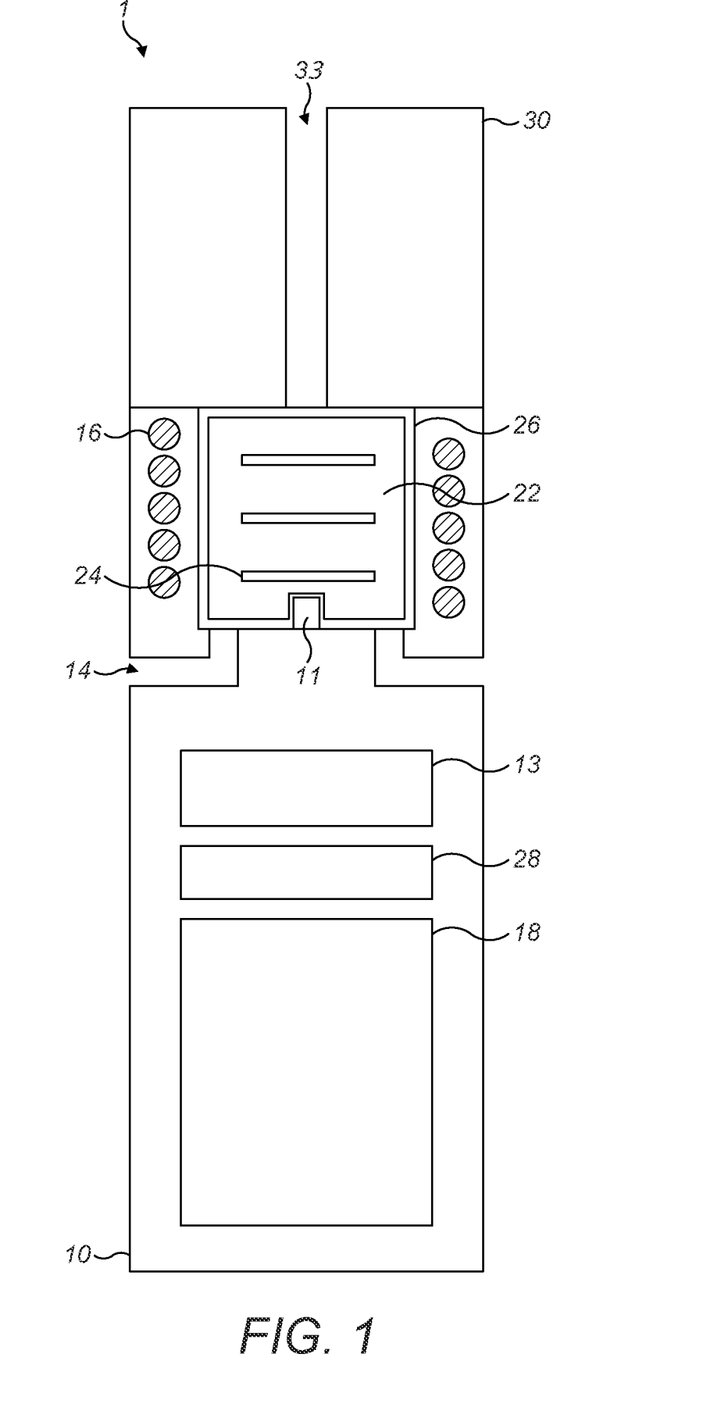
FIG. 1 shows a schematic view of an example vapour generating device.
Figure 2:
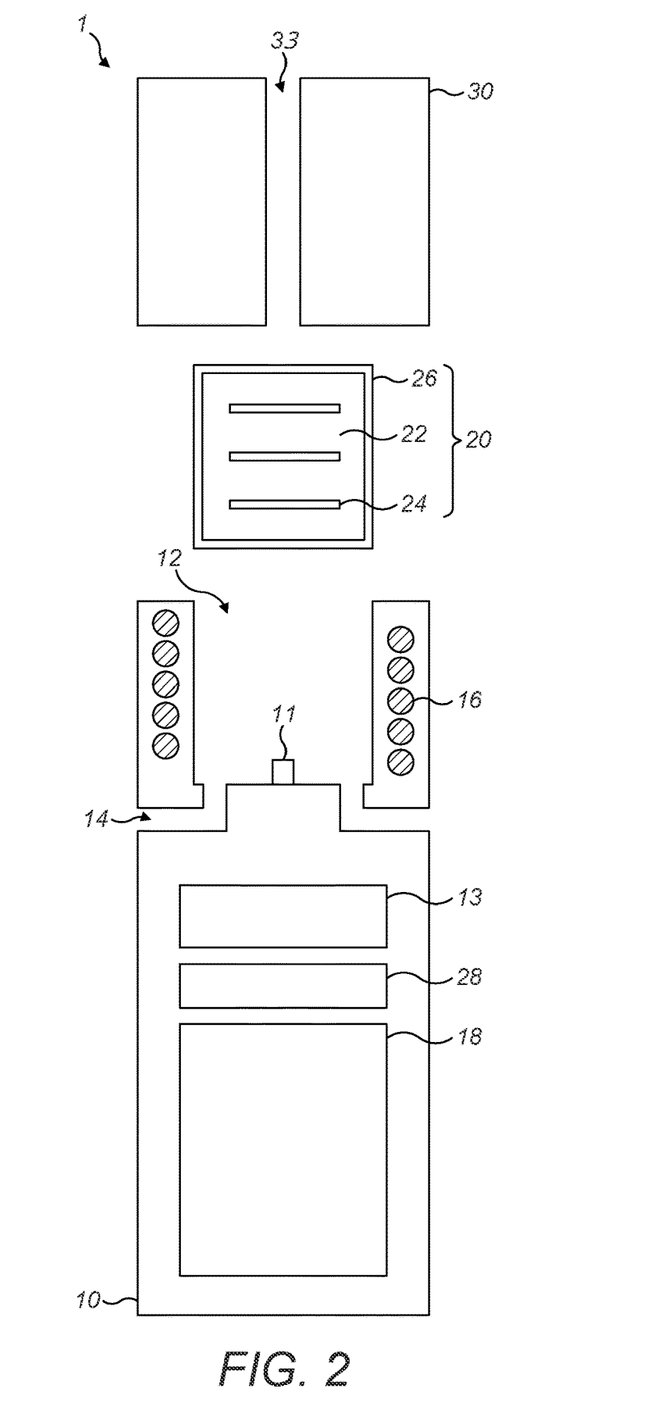
FIG. 2 shows an exploded view of the vapour generating device according to the example shown in FIG. 1.

Referring now to FIG. 1 and FIG. 2, an example vapour generating device is generally illustrated at 1 in an assembled configuration in FIG. 1 and an unassembled configuration in FIG. 2.

The example vapour generating device 1 is a hand held device (by which we intend to mean a device that a user is able to hold and support un-aided in a single hand), which has an induction heating assembly 10, an induction heatable cartridge 20 and a mouthpiece 30. Vapour is released by the cartridge when it is heated. Accordingly, vapour is generated by using the induction heating assembly to heat the induction heatable cartridge. The vapour is then able to be inhaled by a user at the mouthpiece.

In this example, a user inhales the vapour by drawing air into the device 1 from the surrounding environment, through or around the induction heatable cartridge 20 and out of the mouthpiece 30 when the cartridge is heated. This is achieved by the cartridge being located in a heating compartment 12 defined by a portion of the induction heating assembly 10, and the compartment being in gaseous connection with an air inlet 14 formed in the assembly and an air outlet 33 in the mouthpiece when the device is assembled. This allows air to be drawn through the device by application of negative pressure, which is usually created by a user drawing air from the air outlet.

The cartridge 20 is a body which includes a vaporisable substance 22 and an induction heatable susceptor 24. In this example the vaporisable substance includes one or more of tobacco, humectant, glycerine and propylene glycol. The vaporisable substance is also solid. The susceptor includes a plurality of plates that are electrically conducting. In this example, the cartridge also has a layer or membrane 26 to contain the vaporisable substance and susceptor, with the layer or membrane being air permeable. In other examples, the membrane is not present.

As noted above, the induction heating assembly 10 is used to heat the cartridge 20. The assembly includes an induction heating device, in the form of an induction coil 16 and a power source 18. The power source and the induction coil are electrically connected such that electrical power may be selectively transmitted between the two components.

In this example, the induction coil 16 is substantially cylindrical such that the form of the induction heating assembly 10 is also substantially cylindrical. The heating compartment 12 is defined radially inward of the induction coil with a base at an axial end of the induction coil and side walls around a radially inner side of the induction coil. The heating compartment is open at an opposing axial end of the induction coil to the base. When the vapour generating device 1 is assembled, the opening is covered by the mouthpiece 30 with an opening to the air outlet 33 being located at the opening of the heating compartment. In the example shown in the figures, the air inlet 14 has an opening into the heating compartment at the base of the heating compartment.

A temperature sensor 11 is located at the base of the heating compartment 12. Accordingly, the temperature sensor is located within the heating compartment at the same axial end of the induction coil 16 as the base of the heating compartment. This means that when a cartridge 20 is located in the heating compartment and when the vapour generating device 1 is assembled (in other words when the vapour generating device is in use or ready for use) the cartridge is deformed around temperature sensor. This is because, in this example, the temperature sensor does not pierce the membrane 26 of the cartridge due to its size and shape.

The temperature sensor 11 is electrically connected to a controller 13 located within the induction heating assembly 10. The controller is also electrically connected to the induction coil 16 and the power source 18, and is adapted in use to control operation of the induction coil and the temperature sensor by determining when each is to be supplied with power from the power source.

Figure 3:
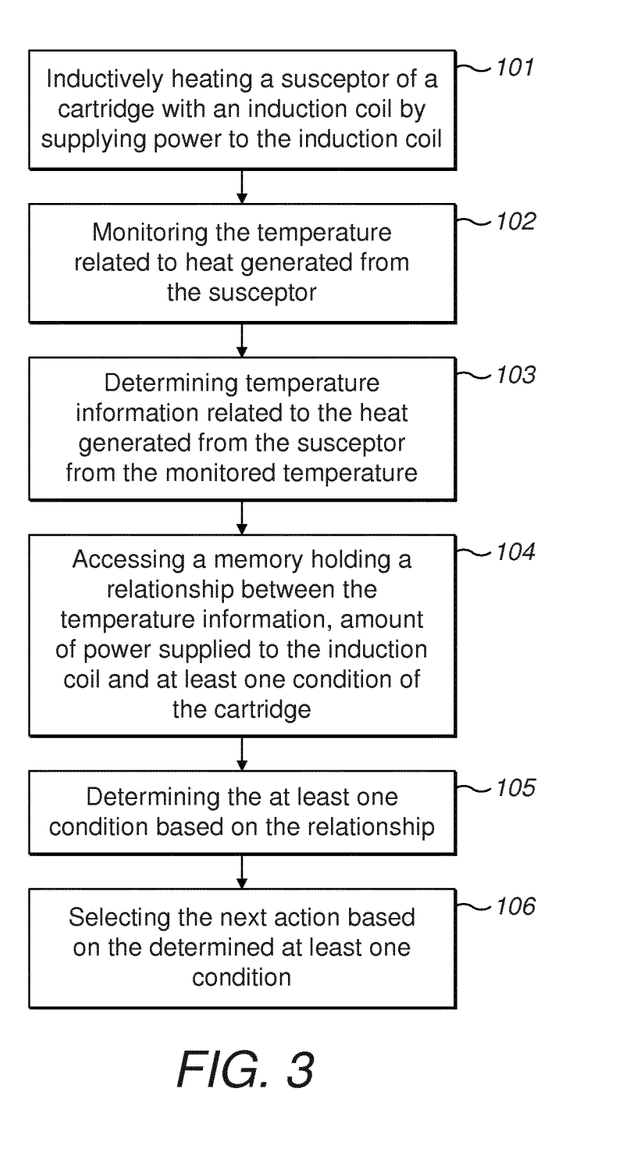
FIG. 3 shows a flow diagram of an example process.

An example process as shown in FIG. 3 is now described. As mentioned above, in order for vapour to be produced, the cartridge 20 is heated, step 101. This is achieved by a direct electrical current supplied by the power source 18 being converted to an alternating current (AC) which is in turn fed to the induction coil 16. The current flows through the induction coil causing a controlled EM field to be generated in a region near the coil. The EM field generated provides a source for an external susceptor (in this case the susceptor plates of the cartridge) to absorb the EM energy and convert it to heat, thereby achieving induction heating.

In more detail, by power being provided to the induction coil 16 a current is caused to pass through the induction coil, causing an EM field to be generated. As mentioned above, the current supplied to the induction coil is an alternating (AC) current. This causes heat to be generated within the cartridge because, when the cartridge is located in the heating compartment 12, it is intended that the susceptor plates are arranged (substantially) parallel to the radius of the induction coil 16 as is shown in the figures, or at least have a length component parallel to the radius of the induction coil. Accordingly, when the AC current is supplied to the induction coil while the cartridge is located in the heating compartment, the positioning of the susceptor plates causes eddy currents to be induced in each plate due to coupling of the EM field generated by the induction coil to each susceptor plate. This causes heat to be generated in each plate by induction.

The plates of the cartridge 20 are in thermal communication with the vaporisable substance 22, in this example by direct or indirect contact between each susceptor plate and the vaporisable substance. This means that when the susceptor 24 is inductively heated by the induction coil 16 of the induction heating assembly 10, heat is transferred from the susceptor 24 to the vaporisable substance 22, to heat the vaporisable substance 22 and produce a vapour.

When the temperature sensor 11 is in use, it monitors the temperature, step 102 by measuring temperature at its surface. Each temperature measurement is sent to the controller 13 in the form of an electrical signal. The controller is then able to process the electrical signal to obtain temperature information, step 103, related to heat generated from the susceptor. In this example, the temperature information includes one or more of the monitored temperature, the surface temperature of the cartridge 20 (which, as noted above, can be the monitored temperature) or the rate of change of temperature.

The controller 13 is also able to monitor the amount of power supplied by the power source 18 to the induction coil 16.

In this example the vapour generating device 1 also has a memory 28. Data is stored in the memory that represents a relationship between the temperature information, the amount of power supplied to the induction coil 16 and at least one condition of the cartridge. Accordingly, the memory holds the relationship. In this example, the at least one condition is one or more of an age of the cartridge 20, a type of the cartridge or whether a cartridge is present or not in the heating compartment 12.

In an alternative example the memory is located on an external device or is located in the cloud, by which we mean internet based computer storage and processing resources that are accessible on demand. In such as case, the vapour generating device has a memory accessor that is able to access and interact with the memory.

In use, the controller 13 is able to access the memory 28, step 104, to retrieve sufficient information to be able to determine, step 105, the at least one condition of the cartridge 20 based on the relationship by conducting processing using the temperature information and the amount of power supplied to the induction coil 16.

As an example of the relationship, for a cartridge containing tobacco, when heated the tobacco in the cartridge generates an aerosol. At the same time as the aerosol is created, the moisture level of the tobacco decreases due to the generation of the aerosol. Therefore, tobacco stored in an unused cartridge and tobacco stored in a used cartridge has different moisture levels, which may be determined by quantity of humectant (providing an aerosol former for example) and water. This has an impact on the rate of change in temperature as the cartridge is heated. For a used capsule, because of the reduced moisture level, such a cartridge heats up more quickly than an unused cartridge heated under the same conditions, so the rate of change of temperature is larger for a used cartridge than for an unused cartridge. Similarly, the amount of power required to heat a used cartridge to a particular temperature is less than for an unused cartridge. This of course also means that a used cartridge is able to be heated to a higher temperature than an unused cartridge when the same amount of power is supplied to the induction coil to provide heating.

A further example of the relationship is that the type of cartridge being heated is able to be determined. Due to differences between types of cartridge, such as differences in the composition of different cartridge types, supplying a particular amount of power to heat a cartridge heats different cartridge types to different temperatures. As such, if a surface temperature of a cartridge is within one temperature range, or is below a particular temperature threshold, the cartridge is able to be determined as one type of cartridge; if the surface temperature of the cartridge is within a second temperature range, or is between two temperature thresholds, then the cartridge is able to be determined as a second type of cartridge; if the surface temperature of the cartridge is within a third temperature range, is between two further temperature thresholds or is below or above a further temperature threshold, then the cartridge is able to be determined as a further type of cartridge.

Another example of the relationship is that whether a cartridge is present in the heating compartment is able to be determined. In this example, if power is supplied to the induction coil and the temperature remains below a temperature threshold, then no cartridge is present. On the other hand, if power is supplied to the induction coil and the temperature increases to or above the temperature threshold, then a cartridge is present. This aspect of the relationship exists because heat is generated by the susceptor in the cartridge, so if the cartridge is not present in the heating compartment, not heat will be produced since there will be no susceptor to generate heat, whereas if a cartridge is present there will be a susceptor to generate heat.

Of course, all three of the examples of the relationship described above are able to be determined at the same time. For example, if no cartridge is present, then the temperature able to be monitored will be below a first threshold temperature. If the temperature is between the first threshold temperature and a second threshold temperature of a higher temperature than the first threshold temperature, then the cartridge is an unused cartridge of a first type. If the temperature is between the second threshold temperature and a third threshold temperature of a higher temperature than the second threshold temperature, the cartridge is an unused cartridge of a second type. If the temperature is between the third threshold temperature and a fourth threshold of a temperature higher than the third threshold temperature, then the cartridge is an unused cartridge of third type of cartridge. If the temperature is above the fourth threshold temperature, then the cartridge is a used cartridge.

Once the at least one condition of the cartridge 20 is determined, the controller 13 selects the next action, step 106, to be carried out by the vapour generating device 1 based on the at least once condition. An example of the next action is to prohibit power being supplied to the induction coil 16 if the cartridge is used. This stops cartridges which are no longer suitable for heating from being used. Of course, the cartridge is able to be used more than a single use before it is determined as being a "used" cartridge. The amount of use a cartridge is exposed to before it is deemed to no longer be suitable is determined, for example, by the predetermined threshold temperature for used cartridges and when a cartridge reaches that temperature when heated from ambient temperature, the cartridge is considered to be "used". This allows cartridges to be used for a sustained time before being considered no longer suitable for heating.

Of course, if a cartridge 20 is determined as being unused, then the controller selects the next action as being supplying power to the induction coil 16 on demand.

In some examples, the vapour generating device 1 has an indicator or display (not shown) that indicates to the user the at least one condition of the cartridge 20 determined by the controller 13.

Figure 4:
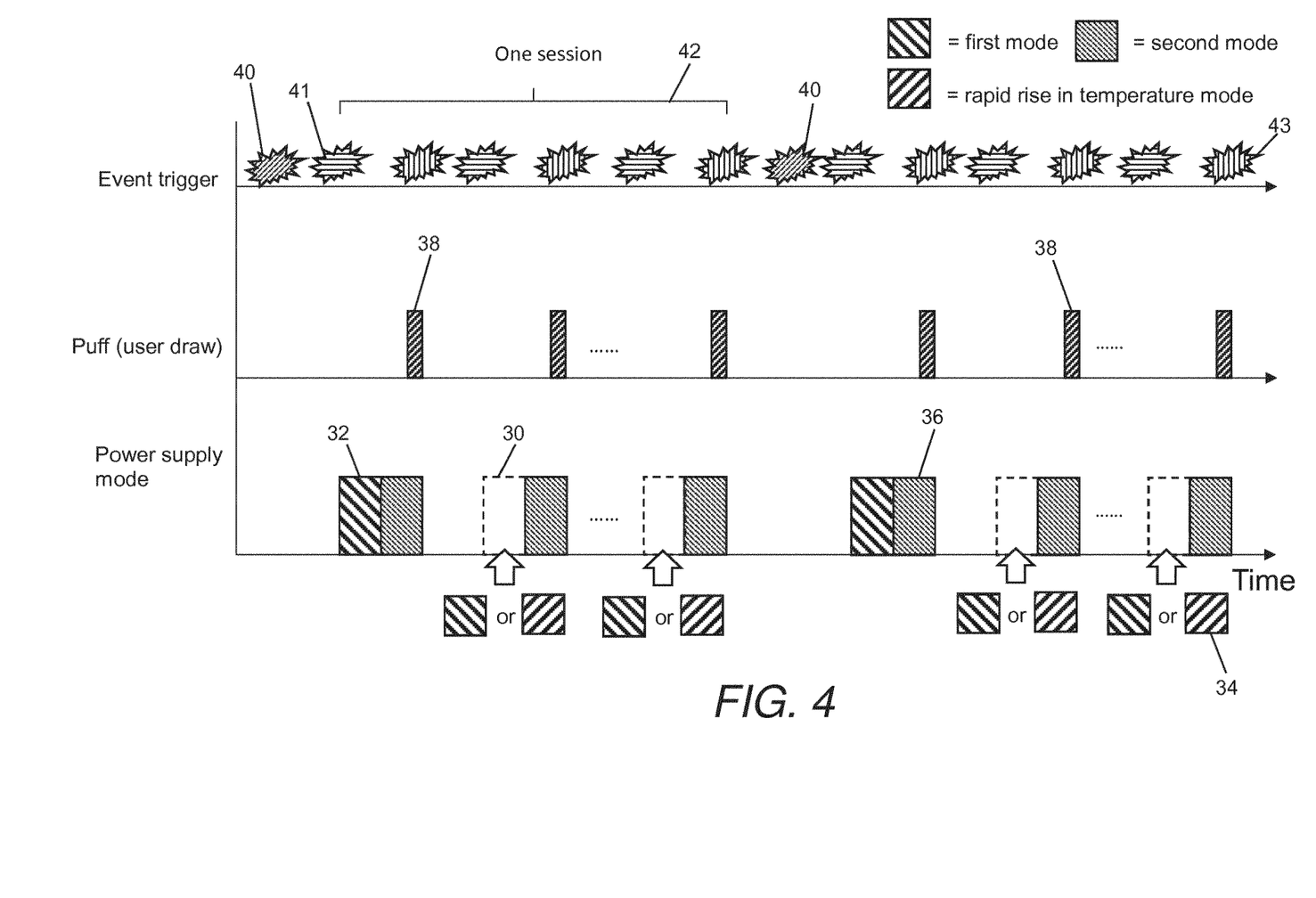
FIG. 4 shows a graph of example power supply modes being applied over time.

FIG. 4 shows an example of how the vapour generating device 1 operates over time. When a user uses the device, there is an initial time period 30 in which the device operates in one of two power supply modes, a first power supply mode 32 or a rapid rise in temperature power supply mode 34. These power supply modes cause the monitorable temperature to be raised to a predetermined temperature, at which point, as long as certain criteria are met (which are described in more detail below), the device changes from operating in the first power supply mode or the rapid rise power supply mode to a second power supply mode 36, which maintains the monitorable temperature within a predetermined temperature range for the remainder of the time that the user uses the device in a single use (a puff 38). Alternately, in some cases, after a time period where the device is in the first power supply mode, the device may continue in the second power supply mode during one session 42. In this case, for example, the second power supply mode continues even during a no-puff time period (similar to the operation set out in FIG. 5). However of course, if the puff does not happen for a predetermined time period, the second power supply mode may finish and then some trigger, such as the next trigger, may start the first power supply mode again.

The first power supply mode 32 differs from rapid rise power supply mode 34 in that only when the device is in the first power supply mode, in addition to increasing the monitorable temperature to the predetermined temperature, the amount of power supplied to the induction coil 16 during this time period is monitored, and temperature information is obtained. The at least one condition of the cartridge 20 that is being heated is then determined from this. Each of the first power supply mode and the rapid rise power supply mode supply power to the induction coil at a rate of at least 80% of the maximum capacity at which the device is able to supply power to the induction coil. This heats up the cartridge quickly so the user experiences as little lag as possible between seeking to use the device and the device working as they expect.

This process is carried out each time the user makes use of the device 1 (i.e. each time the user makes a puff 38), with each use, being determined by a user draw 38 on the mouthpiece 30 of the device. However, the change to the second power supply mode 36 is only carried out when the cartridge is not determined as being a used cartridge. When the cartridge is determined as being a used cartridge, the device is prohibited from changing to the second power supply mode. Alternately, in some cases, based on the detected condition, the controller changes the heating profile (including stopping heating) of a later part of first power supply mode, the rapid rise power supply mode 34 and/or the second power supply mode 36 after the determination.

The act that determines whether the device 1 operates in the first power supply mode 32 or the rapid rise power supply mode 34 is the first use of the device after a trigger 41 during a session 42. The first power supply mode is applied in said first use, and in latter uses, either the first power supply mode or the rapid rise power supply mode are able to be applied.

Each session 42 is intended to be the period of time between consecutive triggers 40. An example trigger includes the push of a button.

In the example shown in FIG. 4, there are additional event triggers. One such event trigger is a change of cartridge trigger 40. In other examples, this trigger may be caused by a different event.

A change of cartridge trigger 40 may be detection of the heating compartment being closed from being open, the insertion of a cartridge or the temperature decreasing due to removal of a cartridge. In this example, a change of cartridge trigger occurring resets the device 1 to applying the first power supply mode at the start of the next session 42 when a trigger 40 (such as the push of a button) occurs and/or resets a counter related to the cartridge, such as the remaining amount of heating time or remaining number of puffs for the cartridge.

Should trigger 40 be a change of cartridge trigger, in this example, this provides a signal that when the next trigger 41 is received the first power supply mode 32 is to be applied when heating starts. Regardless of the type of trigger that trigger 40 provides, this may indicate a session is to start. In some examples, this may be provided by the push of a button. The session then begins when the next trigger 41 is received. The trigger 41 may be provided by any form of event, such as the push of a button. If the trigger 40 is provided by the push of a button, a different type of button push would provide the trigger 41, such as multiple pushes of the button, or a push of the button for at least a predetermined time. In any case, trigger 41 causes heating (and therefore the session) to begin.

A further event trigger of this example is a stop trigger 43. The stop trigger is a detection of the end of a puff (i.e. the end of a draw on the mouthpiece 30, when a user stops drawing). In this example, this causes the second power supply mode to end and thereby causing heating to stop.

Figure 5:
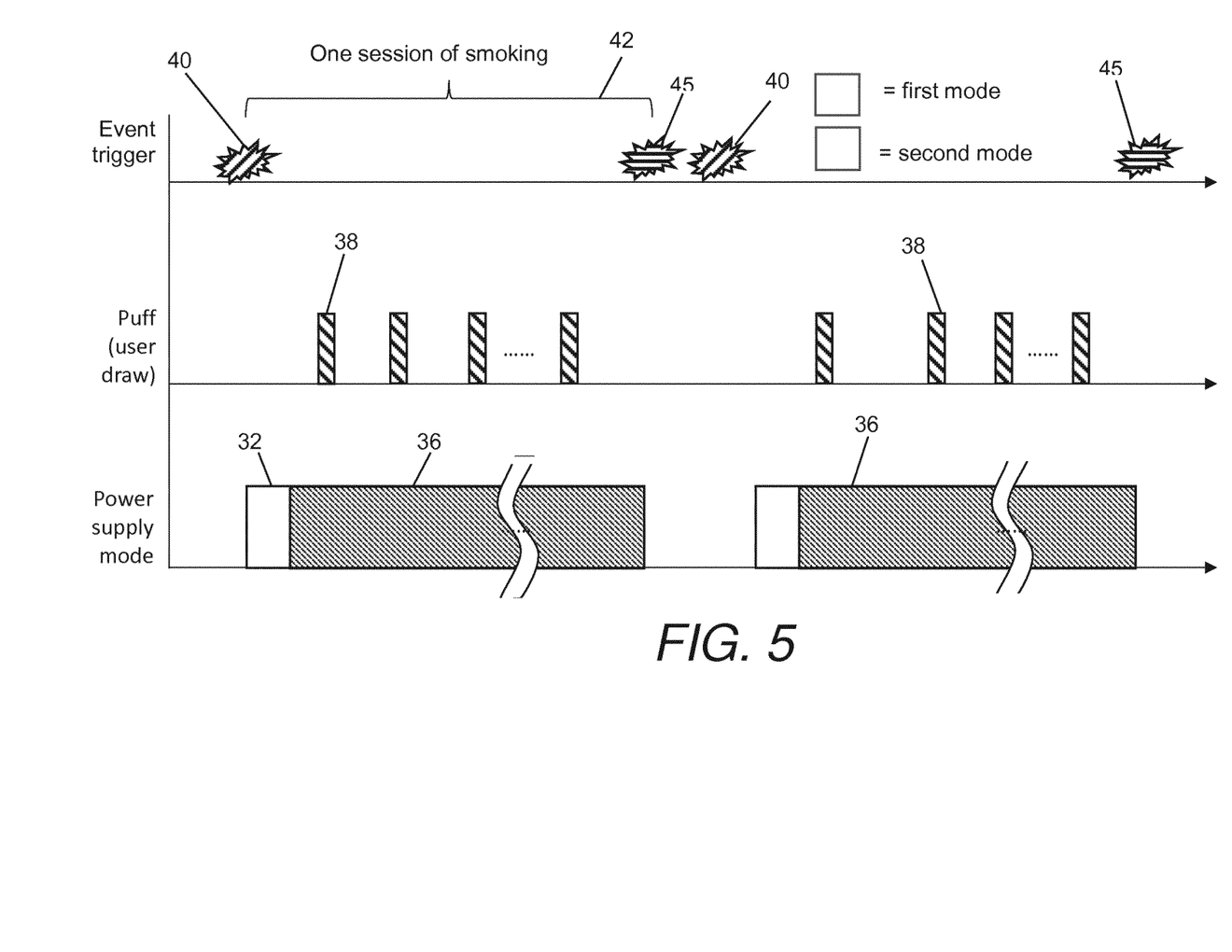
FIG. 5 shows a further graph of example power supply modes being applied over time.

FIG. 5 shows a second example of how the vapour generating device 1 is able to operate over time. When a user uses the device, there is a time period in which the device operates in the first power supply mode 32. As with the example shown in FIG. 4, this power supply mode causes the monitorable temperature to be raised to a predetermined temperature, at which point, as long as certain criteria are met (which are described in more detail below), the device changes from operating in the first power supply mode to a second power supply mode 36. This maintains the monitorable temperature within a predetermined temperature range for the remainder of the time of the session 42. This differs from the example shown in FIG. 4 because the second power supply mode is maintained over the total number of uses (i.e. puffs 38) in the session whether this be one or more puffs. As such, the second power supply mode continues even during a no-puff time period. However of course, if the puff does not happen for a predetermined time period, the second power supply mode may finish and then some trigger, such as the next trigger, may start the first power supply mode again.

As with the example shown in FIG. 4, in the example shown in FIG. 5, the at least one condition of the cartridge 20 that is being heated is then determined from the monitoring the amount of power supplied to the induction coil 16 during the time period the monitored temperature increases to the predetermined temperature, and the temperature information obtained during this time period.

The first power supply mode to the induction coil is at a rate of at least 80% of the maximum capacity at which the device is able to supply power to the induction coil. This heats up the cartridge quickly so the user experiences as little lag as possible between seeking to use the device and the device working as they expect. In a solid-vapour device, if resistive heating is used, in general this time period is more than about 20 seconds. For solid-vapour devices using inductive heating technology, the heating can cause the monitored temperature to be reached within about 3 seconds.

The process of FIG. 5 is carried out each time user starts a session of making use of the device 1 (for example, each time a trigger 40 is received, such as by the push of a button or another event). When such a trigger occurs, this initiates the first power supply mode 32. During the time the device 1 is in the first power supply mode, a determination is carried out to determine if the cartridge is a used cartridge, is not a used cartridge (and so is an unused cartridge) or is not present.

The change to the second power supply mode 36 is only carried out when the cartridge is not determined as being a used cartridge, such as if the cartridge is determined to be a used cartridge or is detected as not being present. When the cartridge is determined as being a used cartridge or not present, the device is prohibited from changing to the second power supply mode. Alternately, in some cases, based on the detected condition, the controller changes the heating profile (including stopping heating) of a later part of first power supply mode, the rapid rise power supply mode 34 and/or the second power supply mode 36 after the determination. The first power supply mode occurs over a short time, such as within three seconds of the trigger 40 being received. The user then draws a puff 38 after the device has moved to the second power supply mode.

The session in the example shown in FIG. 5 ends when a session end trigger 45 occurs. Such a session end trigger occurs, for example, when the remaining amount of time the cartridge can be heated expires. This causes heating to stop.

It is of course possible for the temperature range in which the device is maintained when in the second power supply mode to be varied based on a detected type of cartridge.

In an example, in use a cartridge is removed from the heating compartment of the vapour generating device by a user when it is no longer wanted. A cartridge is then inserted into the heating compartment by a user. To achieve this, the mouthpiece is removed from the rest of the body of the vapour generating device. This causes the heating compartment to be open and the cartridge to be accessible by the user. The cartridge is then pulled from the heating compartment by the user. A cartridge is then placed into the heating compartment by the user and the mouthpiece is reattached to the rest of the body of the vapour generating device.

In embodiments where the mouthpiece is replaced by a cover (not shown) or a cover to the heating compartment is provided in addition to the mouthpiece at an alternate location to the mouthpiece, the cover being able to be articulated backward and forward to open and close the compartment, instead of removing the mouthpiece, the cartridge is removed from the chamber by opening the cover and the user pulling the cartridge through the opening at which the cover is located; said opening of course being in communication with the heating compartment. An alternate cartridge is then able to be introduced into the chamber by inserting it through said opening. The cover is then subsequently closed.

As mentioned above, the trigger is able to be one of a number of events. Taking the example of the trigger being the closing of the heating compartment, when this is detected (such as by a sensor in the vapour generating device), the controller is adapted to cause the first power supply mode to be applied when heating is applied for the first time due to the user seeking to use the vapour generating device.

Figure 6:
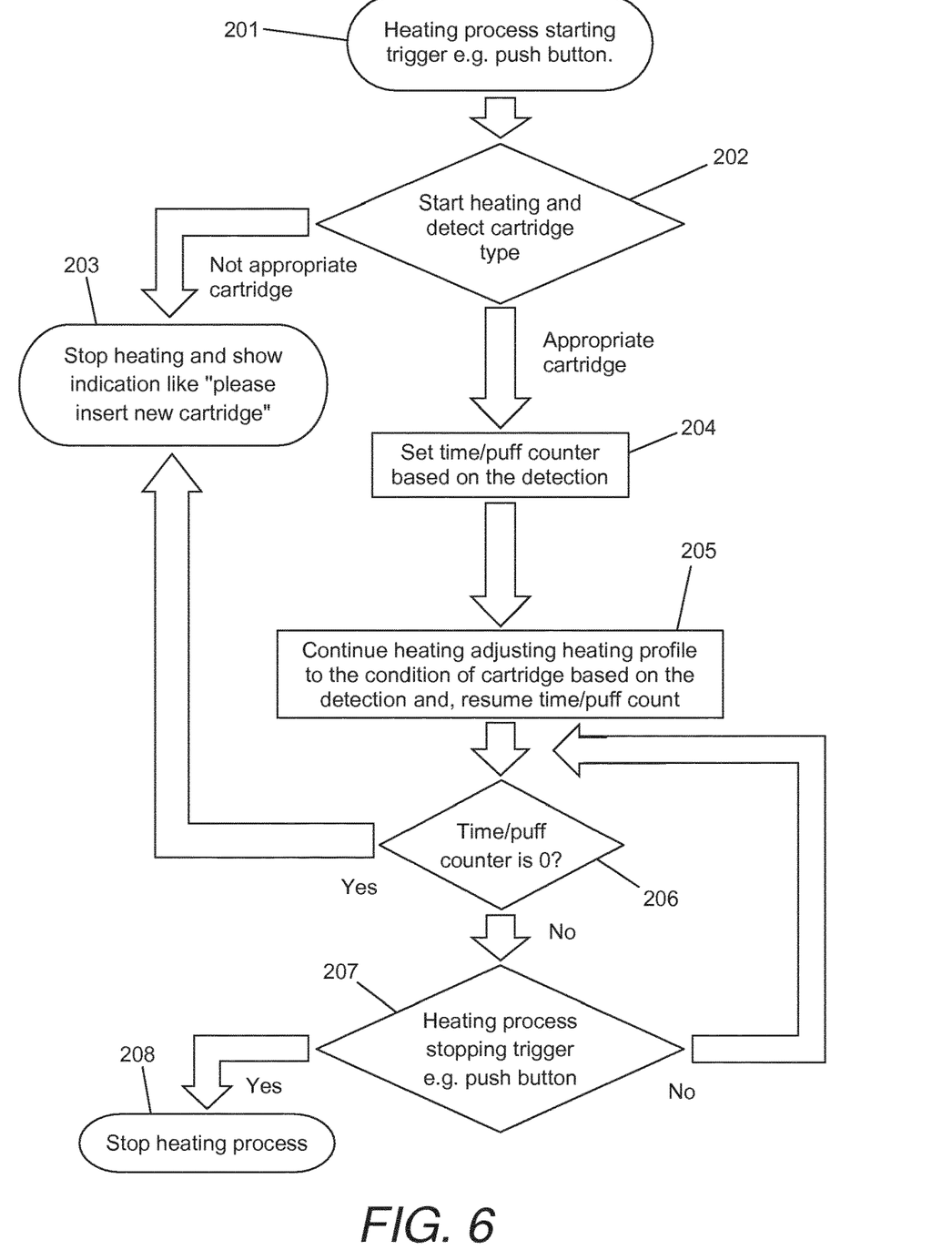
FIG. 6 shows a flow diagram of an example process.

FIG. 6 shows an example process able to be carried out using the vapour generating device described above. When a user starts a session of use of the device, a heating process is started by a trigger event (step 201). The trigger event may for example be a push of a button by a user. As set out above, in other examples, the trigger may be one of a number of events.

The session may be a session using a cartridge that has previously been used or may be a cartridge that has not been used, such as a new cartridge, or a cartridge that is being used in the device for the first time. In the case the sessions is a session using a cartridge that has previously been used in the heating compartment of the device, the beginning of the session may be referred to as "restarting" the session. When the session is a session using a cartridge that has not previously been used in the heating compartment, and so is new to the device, then beginning of the session may be referred to as "starting" the session.

Whether the session is being started or restarted, as mentioned above, a heating process is started. In one example, this involves providing a known amount of power at a low power level to cause heating of the cartridge for a predetermined period of time. The rate of increase in temperature, also referred to as the "temperature ramp rate", is monitored.

Using a process such as the process set out above in relation to FIG. 3, the type and/or age of the cartridge is detected (step 202). In some examples, this involves using a look-up table to compare the monitored temperature ramp rate to a maximum power allowed for later heating of the cartridge, which has been decided based on previously determined test on cartridges of different types, including age, condition and variety.

If the cartridge type detected is not appropriate for the device for any reason, heating is stopped and the device provides an indication to the user (step 203). In this example, the indication may be provided in the form of a message on a display, the message, for example reading "Please insert new cartridge".

When the cartridge type is detected as being an appropriate cartridge type, the remaining heating time or number of remaining puffs is set based on the cartridge type and/or age detected (step 204). Preferably steps 202, 204 and 205 are conducted in first power supply mode. As the session continues, the device moves from the starting heating mode to a normal operating heating mode, such as the second power supply mode. At this time, the maximum power level suitable for the cartridge is applied. The maximum power level to provide heating is adjusted based on the condition of the cartridge as it changes (step 205). This adjustment of the heating profile is based on the remaining time or remaining number of puffs available for the cartridge, and is achieved by a memory accessible by the device being checked to determine the appropriate power amount, such as a maximum permissible power level, to be applied to a cartridge with that amount of usage time/number of remaining puffs.

While the normal operating heating mode continues, the time remaining for the cartridge to be heated is monitor and/or the number of puffs for the cartridge is monitored. A check is run to ascertain if the remaining time or remaining puffs has reached zero (step 206). If the remaining time or remaining puffs has reached zero, then heating is stopped and the device provides an indication to the user (step 203). The indication to the user may be the same as when the cartridge is detected as not being the appropriate type for the device.

If the remaining time or puff count has not reached zero, a check is run to ascertain if a stop trigger for the heating process has been received (step 207). In some examples, the stop trigger is provided by the user pushing a button, which may be the same button as the button that provides the start trigger. If the stop trigger is received then heating is stopped (step 208). If no stop trigger has been received, then the process proceeds in a cycle by returning to the check of whether the remaining time or puff count is zero in step 206.

Following heating being stopped, the whole process may be restarted when the next start trigger is received.

The invention claimed is:

1. A heating assembly for a vapour generating device, the heating assembly comprising:
   a heating device arranged to heat, in use, a body, the body comprising a vaporisable substance located in use in a heating compartment of the heating assembly, the heating assembly being arranged to supply, in use, power to the heating device to heat the body or being arranged to supply, in use, power based on a predetermined power supply profile, said predetermined power supply profile being configured to provide a predetermined heating profile to the body;
   a temperature sensor arranged to monitor, in use, a temperature related to heating at the body, temperature information related to heating at the body being determinable from the temperature monitored by the temperature sensor; and
   a memory accessor arranged to access, in use, a memory that holds a relationship between the temperature information, an amount of power supplied to the heating device or the predetermined power supply profile of power supplied to the heating device, and at least one condition, the at least one condition including an age of the body, or a type of the body, or a presence of the body in the heating compartment.

2. The heating assembly according to claim 1, wherein the temperature information includes a rate of change of the monitored temperature.

3. The heating assembly according to claim 1, wherein the temperature information includes a surface temperature of the body.

4. The heating assembly according to claim 1, wherein the at least one condition is determinable from the temperature information and the amount of power supplied to the heating device or the predetermined power supply profile of power supplied to the heating device based on the relationship held in the memory.

5. The heating assembly according to claim 4, wherein the at least one condition is able to be determined based on a threshold temperature for the temperature information.

6. The heating assembly according to claim 4, wherein at least two of the age of the body, the type of the body, and the presence of the body in the heating compartment are determinable at the same time.

7. The heating assembly according to claim 1, further comprising a controller arranged to determine, in use, the temperature information related to heating at the body.

8. The heating assembly according to claim 7, wherein, based on the temperature information, the controller is arranged to determine, in use, a next action of the heating assembly.

9. The heating assembly according to claim 8, wherein based on the relationship held in the memory, the controller is arranged to prohibit, in use, supply of power to the heating device when the age of the body is greater than a threshold age, and is arranged to supply, in use, power to the heating device when the age of the body is less than the threshold age or when a type of the body is determined to be an unsuitable type for the heating assembly.

10. The heating assembly according to claim 1, wherein the heating assembly has a first power supply mode and a second power supply mode, and wherein the first power supply mode is arranged to be applied, in use, when heating the body, and the second power supply mode is arranged to be applied, in use, after the first power supply mode is applied, to maintain the body at a temperature within a predetermined temperature range.

11. The heating assembly according to claim 10, wherein the at least one condition is determinable from the temperature information and the amount of power supplied to the heating device or the predetermined power supply profile of power supplied to the heating device in the first power supply mode based on the relationship held in the memory.

12. The heating assembly according to claim 10, wherein the first power supply mode is arranged to occur in response to a trigger, the trigger being determined based on a change in the monitored temperature or a change in a switch caused by action of a user.

13. A heating assembly for a vapour generating device, the heating assembly comprising:
a heating device arranged to heat, in use, a body, the body comprising a vaporisable substance located in use in a heating compartment of the heating assembly, the heating assembly being arranged to supply, in use, power to the heating device to heat the body or being arranged to supply, in use, power based on a predetermined power supply profile, said predetermined power supply profile being configured to provide a predetermined heating profile to the body;
a temperature sensor arranged to monitor, in use, a temperature related to heating at the body, temperature information related to heating at the body being determinable from the temperature monitored by the temperature sensor; and
a memory accessor arranged to access, in use, a memory that holds a relationship between the temperature information, an amount of power supplied to the heating device or the predetermined power supply profile of power supplied to the heating device, and at least one condition, the at least one condition including an age of the body, or a type of the body, or a presence of the body in the heating compartment
wherein the heating assembly is an induction heating assembly, the heating device is an induction heating device, the body further comprising an induction heatable susceptor, the induction heating device being arranged to heat, in use, the induction heatable susceptor of the body, the heating assembly being arranged to supply, in use, power to the induction heating device to heat the induction heatable susceptor, the temperature sensor being arranged to monitor, in use, a temperature related to heat generated from the susceptor, temperature information related to heat generated from the susceptor being determinable from the monitored temperature.

14. A method for determining a condition of a body, the body comprising a vaporisable substance, the method comprising:
heating the body with a heating device by supplying power to the heating device;
monitoring a temperature related to heating at the body, temperature information related to heating at the body being determinable from the temperature monitored;
accessing a memory, the memory holding a relationship between the temperature information, an amount of power supplied to the heating device or a power supply profile of power supplied to the heating device and at least one condition, the at least one condition including an age of the body, or a type of the body, or a presence of the body in a heating compartment of the heating assembly, when applied said power supply profile provides a predetermined heating profile to the body; and
determining the at least one condition based on the relationship held in the memory.

15. The method according to claim 14, further comprising setting a remaining heating amount for the body based on a relationship between the temperature information, the amount of power supplied to the heating device or the power supply profile of power supplied to the heating device and the age of the body in the memory.

16. The method according to claim 14, further comprising determining a maximum permissible power level for the body based on a relationship between the temperature information, the amount of power supplied to the heating device or the power supply profile of power supplied to the heating device and the age of the body in the memory.

17. A vapour generating device comprising:
the heating assembly according to claim 1;
a heatable body located within the heating compartment of the heating assembly, the heatable body comprising a vaporisable substance of solid or semi-solid material;
an air inlet arranged to provide air to the heating compartment; and an air outlet in communication with the heating compartment.

18. The heating assembly according to claim 5, wherein there are a plurality of threshold temperatures, at least one of the plurality of threshold temperature determining the age of the body, at least one of the plurality of threshold temperature determining the type of the body, and at least one of the plurality of threshold temperature determining the presence of the body in the heating compartment.

19. The heating assembly according to claim 10, wherein when in the first power supply mode, the heating assembly is arranged to provide at least 80 percent (%) of full power to the heating device.

* * * * *